(12) United States Patent
Waite (10) Patent No.: US 6,281,357 B1
(45) Date of Patent: Aug. 28, 2001

(54) PROCESS FOR THE PRODUCTION OF INDOLE DERIVATIVES

(75) Inventor: David Charles Waite, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/381,072

(22) PCT Filed: Jun. 16, 1998

(86) PCT No.: PCT/EP98/03996

§ 371 Date: Mar. 24, 2000

§ 102(e) Date: Mar. 24, 2000

(87) PCT Pub. No.: WO99/02493

PCT Pub. Date: Jan. 21, 1999

(30) Foreign Application Priority Data

Jul. 8, 1997 (GB) .................................................. 9714383

(51) Int. Cl.[7] ..................... C07D 209/14; C07D 403/06; C07D 403/14
(52) U.S. Cl. ..................... 544/295; 548/468; 548/503; 548/504
(58) Field of Search ................. 544/295; 548/468, 548/503, 504

(56) References Cited

U.S. PATENT DOCUMENTS 5,037,845 * 8/1991 Oxford .................................. 514/415

FOREIGN PATENT DOCUMENTS

500086 A1 * 8/1992 (EP) .

OTHER PUBLICATIONS

Sammes, M. P.; Wylie, C. M.; Hoggett, J. G, J. Chem. Soc. C (1971), (11), 2151–5.*

* cited by examiner

Primary Examiner—Richard L. Raymond
Assistant Examiner—Thomas McKenzie
(74) Attorney, Agent, or Firm—Peter C. Richardson; Paul H. Ginsburg; Roy F. Waldron

(57) ABSTRACT

The invention provides a process for the production of a compound of formula I, which comprises reacting a compound of formula II with a compound of formula III, in the presence of a strong base and a palladium(0) catalyst, at an elevated temperature, in a solvent which does not adversely affect the reaction. Compounds of formula I may be further processed to compounds of formula V, which are useful in the treatment of inter alia migraine.

15 Claims, 2 Drawing Sheets

PROCESS FOR THE PRODUCTION OF INDOLE DERIVATIVES

This application is the National Stage application of International application No. PCT/EP98/03996, filed Jun. 16, 1998, which claims priority from Great Britain application No. 9714383.8, filed Jul. 8, 1997.

This invention relates to a novel process for the production of a known class of compounds, some of which are known to be pharmacologically active.

For example, International Patent Application WO 92/06973 discloses a series of indole derivatives that are potent serotonin (5-HT) agonists. These compounds are indicated for treating disorders arising from deficient serotonergic neurotransmission comprising hypertension, depression, anxiety, eating disorders, obesity, drug abuse, cluster headache, migraine, pain and chronic paroxysmal hemicrania and headache associated with vascular disorders. The compounds covered by WO 92/06973 include (R)-5-(methylaminosulphonylmethyl)-3-(N-methylpyrrolidin-2-ylmethyl)-1H-indole (Example 5A, known as CP-122,288), which has the following structure:

CP-122,288

UK Patent N° 2,162,522 discloses an indole derivative (known as sumatriptan) which is sold for the treatment of migraine under the trade mark IMIGRAN, and which has the following structure:

Sumatriptan

European Patent Application 0548813 discloses another indole derivative (see Example 29, known as BMS-180048) which is indicated in the treatment of migraine, and which has the following structure:

BMS-180048

In the prior art, synthesis of these compounds begins with a substituted benzyl halide, which then undergoes displacement with a suitable sulphur nucleophile (for example sodium sulphite). The product is then oxidised to the corresponding sulphonyl chloride and condensed with methylamine to give the desired secondary sulphonamide group. The resulting compound then undergoes an intramolecular cyclisation to form the desired indole ring. In the case of CP-122,288, this cyclisation is a Heck reaction according to the following scheme:

wherein P is a protecting group.

Reactions of this type can have a low yield (often around 25%) and result in a mixture of products, which require column chromatography to purify. This makes the production of the desired products expensive and inefficient.

Figure 1:
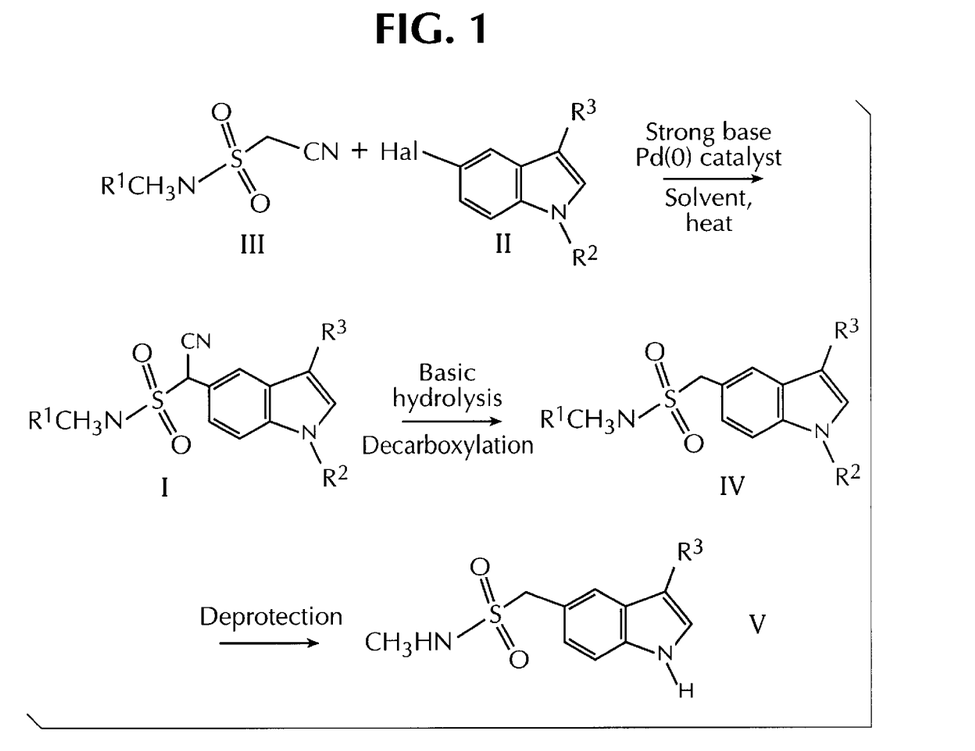
FIG. 1 depicts the process comprising the reaction of a cyano compound of formula III with a halogen-substituted compound of formula II in the presence of a strong base and palladium(0) catalyst to form a compound of formula I followed by basic hydrolysis and decarboxylation to form a compound of formula IV which is then de-protected to form a compound of formula V.

The novel process of the present invention is summarised in accompanying FIG. 1, in which $R^{13}$ and Hal are defined below, and the compounds described above are compounds of formula V.

The process of the present invention utilises a palladium catalysed cross-coupling to introduce the sulphonamidomethylene unit in one portion to a pre-formed indole ring, thus avoiding an intramolecular cyclisation and the problems associated with it, described above. Therefore the process of the present invention has the advantages that it has a higher yield and does not always require column chromatography, in comparison with the prior art.

Sakamoto et al disclose palladium catalysed reactions of phenylsulphonylacetonitrile with various halogen-substituted aromatic compounds. The aromatic compounds concerned did not contain active hydrogen and so did not require protection during the reaction [see Synthesis, 1992, p 552; and Chem Pharm Bull, 38(6), pp 1513–1517 (1990)].

According to a first aspect of the present invention, there is provided a process for the production of a compound of formula I, wherein $R^1$ and $R^2$ independently represent N-protecting groups; and $R^3$ represents a $C_{1-6}$ alkyl group substituted by:
(i) a 5- or 6-membered nitrogen-containing saturated heterocyclic group which in turn may be substituted by $C_{1-6}$ alkyl or a pyrimidine ring which is itself substituted by $C_{1-6}$ alkoxy; or
(ii) di($C_{1-6}$ alkyl)amino;
which comprises reacting a compound of formula II, wherein Hal represents Cl, Br or I; and
$R^2$ and $R^3$ are as defined above;
with a compound of formula III, wherein $R^1$ is as defined above;
in the presence of a strong base and a palladium(0) catalyst, at an elevated temperature, in a solvent which does not adversely affect the reaction.

Preferred strong bases are sodium hydride and potassium t-butoxide.

Preferably, the palladium(0) catalyst is tetrakis(triphenylphosphine)palladium(0). This may be added to the reaction mixture as $Pd(II)Cl_2[P(C_6H_5)_3]_2$, and is converted to the palladium(0) species under the reaction conditions. Similarly, $Pd(II)(O_2CCH_3)_2$ may be added to the reaction mixture and is converted to a palladium(0) species under the reaction conditions.

Suitable solvents include toluene, and, more preferably, a mixture of toluene and ethylene glycol-dimethylether ($CH_3OCH_2CH_2OCH_3$). This latter solvent system has the advantage that the deprotonated compounds of formula III remain mobile in the reaction mixture and so available for reaction.

Preferably, the process is carried out at the reflux temperature of the solvent. In the solvent systems mentioned in the preceding paragraph, this will be approximately 80° C. and 100° C. respectively. At these temperatures, the process should be complete in 1–3 hours.

Preferably, Hal is Br.

According to a second aspect of the present invention, there is provided a process for the production of a compound of formula V, wherein
$R^3$ is as defined above;
which comprises:
(i) basic hydrolysis of the cyano group of a compound of formula I as defined above, followed by decarboxylation of the resulting carboxylic acid, to provide a compound of formula IV, wherein $R^{1-3}$ are as defined above; followed by
(ii) replacement of $R^1$ and $R^2$ with H.

Preferably, step (i) is carried out using aqueous potassium hydroxide in ethanol at an elevated temperature. The aqueous potassium hydroxide is preferably dilute (for example 1–2 M). The reaction is preferably carried out at the reflux temperature of the reaction mixture (typically around 78° C. using the preferred conditions mentioned above). Under these conditions, the reaction is usually complete in 8–16 hours.

Preferably, $R^1$ and $R^2$ are replaced with H under the same conditions in step (ii), but they may be replaced sequentially. A preferred method for their simultaneous replacement is hydrogenolysis. Suitable hydrogenolysis conditions include palladium-on-carbon in the presence of hydrogen gas at a temperature of 60° C. and a pressure of 414 kPa (60 psi); and sodium or calcium in liquid ammonia at –50 to –33° C.

In each aspect of the invention, it is preferred that $R^1$ represents benzyl, $CH_2OCH_2(C_6H_5)$, $CH(C_6H_5)_2$ or t-butyl. $CH_2OCH_2(C_6H_5)$ is of particular interest.

In each aspect of the invention, it is preferred that $R^2$ represents an N-protecting group which is stable to basic hydrolysis conditions, particularly the basic hydrolysis conditions used in step (i) of the second aspect of the invention. It has been found that the basic hydrolysis and decarboxylation of this step is greatly enhanced if $R^2$ remains in place during the reaction. Of course, $R^2$ need not be the same in each aspect of the invention, but selection of a suitable $R^2$ group in compounds of formula II in the first aspect of the invention obviates the need to replace an unstable protecting group for step (i) of the second aspect of the invention, so that the enhancement mentioned above can be achieved. N-protecting groups that are stable to basic hydrolysis conditions include benzyl, $CH_2OCH_2(C_6H_5)$, $CH_2OCH_2CH_2Si(CH_3)_3$ and $CH_2CHCH_2$. However, since they are both removable by hydrogenolysis, benzyl and $CH_2OCH_2(C_6H_5)$ are preferred.

Preferably, $R^3$ represents $CH_2CH_2N(CH_3)_2$ or a group of formula Ia or Ib, The compounds of formula V in which R³ represents these groups are sumatriptan, CP-122,288 and BMS-180048 respectively.

The invention further provides the intermediate compounds of formulae I, III and IV as defined above.

Figure 2:
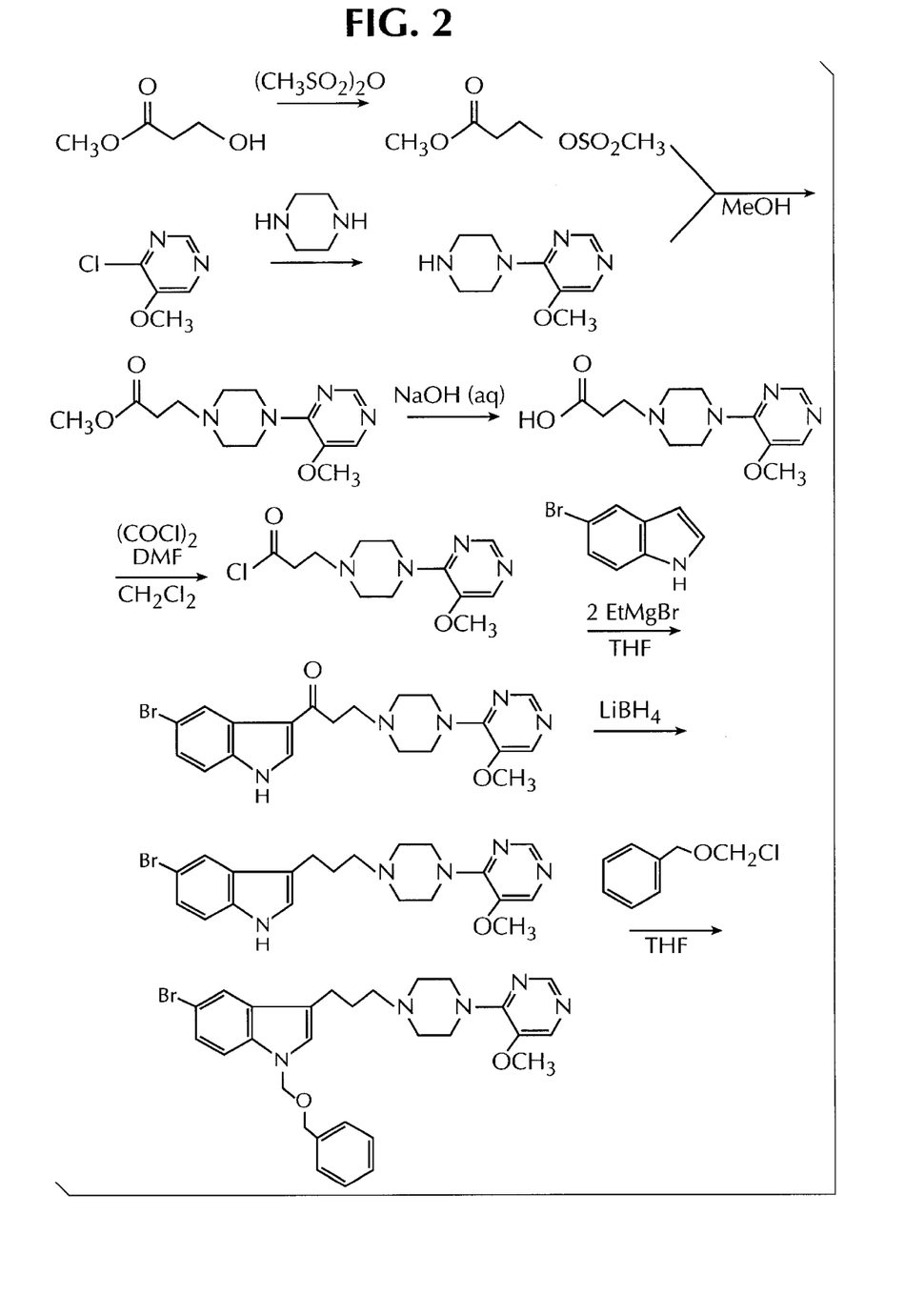
FIG. 2 depicts a process for the preparation of compound of formula II wherein $R^3$ is a 3-[4-(5-methoxy-4-pyrimidinyl)-1-piperazinyl]-propyl group and $R^2$ is a $CH_2OCH_2(C_6H_5)$ group.

Compounds of formulae II and III may be prepared by conventional methods as illustrated in the examples. When R³ is a group of formula Ib and R² represents $CH_2OCH_2$ ($C_6H_5$), the compound of formula II may be prepared as shown in accompanying FIG. 2.

The invention is illustrated by the following Examples, in which the abbreviations set out below may be used:

| | |
|---|---|
| DMF | dimethylformamide |
| Et | ethyl |
| IMS | industrial methylated spirits |
| hr | hour |
| MeOH | methanol |
| min | minute |
| LRMS | low resolution mass spectroscopy |
| THF | tetrahydrofuran |

EXAMPLE 1

(R)-N-Methyl-[3-(1-methyl-2-pyrrolidinylmethyl-1H-indol-5-yl]methanesulfonamide (a) Methyl (N-benzyl-N-methylsulfamoyl)acetate To a stirred solution of N-methyl benzylamine (7 ml, 54.2 mmol) in dichloromethane (10 ml) at 0–5° C. under an atmosphere of nitrogen was added dropwise a solution of methyl chlorosulfonylacetate (prepared by the method of M. J. Szymonifka and J. V. Heck, *Tetrahedron Lett.*, 1989, 30, 22, 2869) (4.26 g, 24.7 mmol) in dichloromethane (5 ml), maintaining the temperature below 5° C. The yellow solution was then warmed to ambient temperature over a 2 hr period before water (30 ml) was added. The organic phase was partitioned and evaporated in vacuo to give a yellow oil. This was purified by flash column chromatography (diethyl ether:hexane 1:1 as eluant) to give the subtitle compound (3.9 g, 61%) as a colourless oil.

¹H NMR (300 MHz, CDCl₃) δ=2.83 (3H, s), 3.83 (3H, s), 4.02 (2H, s), 4.38 (2H, s), 7.27–7.42 (5H, m).

Found: C, 51.31; H, 5.92; N, 5.42. $C_{11}H_{15}NO_4S$ requires C, 51.35; H, 5.88; N, 5.44%.

(b) (N-Benzyl-N-methylsulfamoyl)acetamide

To a stirred solution of methyl (N-benzyl-N-methylsulfamoyl)acetate (from step (a), 3.9 g, 15.2 mmol) in tetrahydrofuran (10 ml) at ambient temperature was added aqueous ammonia (10 ml, s.g.=0.88) in one portion. The orange solution was then stirred at ambient temperature for 18 hr, before being poured into water (50 ml) and extracted with ethyl acetate (3×25 ml). The organic extract was evaporated in vacuo to give the subtitle compound (2.8 g, 76%) as a white solid. m.p. 124–127° C.

¹H NMR (300 MHz, CDCl₃) δ=2.83 (3H, s), 3.92 (2H, s), 4.39 (2H, s), 5.61 (1H, bs), 6.50 (1H bs), 7.20–7.45 (5H, m).

Found: C, 49.56; H, 5.78; N, 11.54. $C_{10}H_{14} N_2O_3S$ requires C, 49.57; H, 5.82; N, 11.56%.

(c) N-Benzyl-1-cyano-N-methylmethanesulfonamide

The subtitle compound (2.36 g, 91%) was prepared as a white solid from (N-benzyl-N-methylsulfamoyl)acetamide (from step (b), 2.8 g, 11.6 mmol) according to the procedure of Bargar and Riley (*Synthetic Communications*, 1980, 10 (6), 479). m.p. 68–70° C. ¹H NMR (300 MHz, CDCl₃) δ=2.95 (3H, s), 3.96 (2H, s), 4.50 (2H, s), 7.10–7.53 (5H, m).

Found: C, 53.41; H, 5.36; N, 12.39. $C_{10}H_{12}N_2O_2S$ requires C, 53.55; H, 5.39; N, 12.49%.

(d) (R)-1-Benzyl-5-bromo-3-(1-methyl-2-pyrrolidinylmethyl)-1H-indole

To a stirred solution of (R)-5-bromo-3-(1-methyl-2-pyrrolidinylmethyl)-1H-indole (see Example 27, WO 92/06973) (21.44 g, 73.2 mmol) in tetrahydrofuran (110 ml) at 0° C. under a nitrogen atmosphere was added sodium hydride (60% dispersion in mineral oil, 3.51 g, 87.7 mmol) portionwise, maintaining the temperature below 5° C. Upon completion of the addition, the dark brown solution was stirred at 0–5° C. for 1 hr before benzyl bromide (10.4 ml, 87.4 mmol) was added dropwise maintaining the temperature below 5° C. The brown solution was then warmed to ambient temperature over a 1 hr period before being quenched into water (100 ml). The mixture was then extracted with ethyl acetate (3×25 ml) and the organic extracts were combined and evaporated in vacuo to yield a brown oil. This was purified by flash column chromatography (ethyl acetate:hexane:diethylamine 1:1:0.1 as eluant) to give the subtitle compound (17.6 g, 63%) as a brown viscous oil.

$^1$H NMR (300 MHz, CDCl$_3$) δ=1.50–1.95 (4H, m), 2.19–2.35 (1H, m), 2.49 (4H, m), 2.56–2.70 (1H, m), 3.10–3.25 (2H, m), 5.20 (2H, s), 6.99 (1H, s), 7.03–7.16 (3H, m), 7.20–7.37 (4H, m), 7.69 (1H, s).

Found: C, 65.83; H, 6.08; N, 7.24. $C_{21}H_{23}BrN_2$ requires C, 65.80; H, 6.05; N, 7.31%. [α]$_D$+64.30° (c=1.78, MeOH).

(e) N-Benzyl-1-[(R)-1-benzyl-3-(1-methyl-2-pyrrolidinylmethyl)-1H-indol-5-yl]-1-cyano-N-methylmethanesulfonamide

To a stirred solution of N-benzyl-1-cyano-N-methylmethanesulfonamide (from step (c), 643 mg, 2.9 mmol) in toluene (5 ml) at 0° C. under a nitrogen atmosphere was added potassium tert-butoxide (615 mg, 5.5 mmol) portionwise, maintaining the temperature below 5° C. The brown solution was then warmed to ambient temperature over a 10 min period, before tetrakis(triphenylphosphine) palladium(0) (181 mg, 0.16 mmol) was added in one portion. A solution of (R)-1-benzyl-5-bromo-3-(1-methyl-2-pyrrolidinylmethyl)-1H-indole (from step (d), 1.0 g, 2.6 mmol) in toluene (5 ml) was then added dropwise to the yellow slurry and the mixture was warmed to reflux. Reflux was maintained for 1.5 hr after which time the dark brown solution was cooled to ambient temperature. The reaction mixture was then poured into water (25 ml) and extracted with ethyl acetate (3×25 ml). The combined organic extracts were evaporated in vacuo to yield a brown oil. This was purified by flash column chromatography (ethyl acetate:hexane:diethylamine 1:1:0.1 as eluant) to give the title compound (1.09 g, 80%) as a brown oil.

$^1$H NMR (300 MHz, CDCl$_3$) δ=1.49–1.90 (4H, m), 2.16–2.30 (1H, m), 2.35–2.55 (4H, m), 2.62–2.81 (4H, m), 3.08–3.26 (2H, m), 4.18 (2H, s), 5.26 (1H, s), 5.31 (2H, s) 7.02–7.13 (3H, m), 7.20–7.41(10H, m), 7.81(1H, bs).

Found: C, 69.94; H, 6.56; N, 10.23. $C_{31}H_{34}N_4O_2S$ requires C, 70.7; H, 6.51; N, 10.64%.

(f) (R)-N-Benzyl-1-[1-benzyl-3-(1-methyl-2-pyrrolidinylmethyl)-1H-indol-5-yl]-N-methylmethanesulfonamide To a stirred solution of N-benzyl-1-[(R)-1-benzyl-3-(1-methyl-2-pyrrolidinylethyl)-1H-indol-5-yl]-1-cyano-N-methylmethanesulfonamide (from step (e), 29 g, 55.1 mmol) in ethanol (200 ml) at ambient temperature was added 2N potassium hydroxide solution (200 ml, 400 mmol). The dark brown solution was then brought to reflux and maintained at this temperature for 15 hr. The oily reaction mixture was then cooled to ambient temperature and extracted with ethyl acetate (3×300 ml). The organic extracts where combined and evaporated in vacuo to give a dark brown oil. This was purified by flash column chromatography (ethyl acetate:hexane:diethylamine 1:1:0.1 as eluant) to yield the subtitle compound (24.67 g, 89%) as a brown oil.

$^1$H NMR (300 Mhz, CDCl$_3$) δ=1.54–1.98 (4H, m), 2.18–2.35 (1H, m), 2.40–2.86 (8H, m), 3.09–3.30 (2H, m), 4.03 (2H, s), 4.42 (2H, s), 5.28 (2H, s) 6.99–7.44 (13H, m), 7.64 (1H, s).

Found: C, 70.99; H, 7.07; N, 8.10. C$_{30}$H$_{35}$N$_3$O$_2$S requires C, 71.82; H, 7.04; N, 8.38%. [α]$_D$ +50.98° (c=1.55, CH$_2$Cl$_2$.

(g) (R)-N-Methyl-[3-(1-methyl-2-pyrrolidinylmethyl)-1H-indol-5-yl]methanesulfonamide

A solution of (R)-N-Benzyl-1-[1-benzyl-3-(1-methyl-2-pyrrolidinylmethyl)-1H-indol-5-yl]-N-methylmethanesulfonamide (from step (f), 2.04 g) in tetrahydrofuran (2 ml) was added dropwise to liquid ammonia (10 ml) at −40° C. under a nitrogen atmosphere. Sodium (approximately 500 mg) was then added portionwise to the colourless solution, until a permanent dark blue coloured solution was obtained. The blue solution was stirred for a further 30 min at −40° C. before saturated ammonium chloride solution (5 ml) was added and the grey slurry warmed to ambient temperature over an 8 hr period. The white slurry was then diluted with water (10 ml), filtered and dried in vacuo at 50° C. to give the title compound (733 mg, 56%) as a white solid. m.p. 209–213° C.

$^1$H NMR (300 MHz, DMSO) δ=1.36–1.81 (4H, m), 2.04–2.17 (1H, m), 2.28–2.52 (8H, m), 2.90–3.09 (2H, m), 4.34 (2H, s), 6.74–6.83 (1H, m), 7.07 (1H, d, J=9.7 Hz), 7.15 (1H, bs), 7.30 (1H, d, J=9.7 Hz), 7.51 (1H, s), 10.85 (1H, bs). LRMS (Thermospray): 322 (MH$^+$). [α]$_D$ +81.08° (c=0.47, DMSO).

EXAMPLE 2

(R)-N-Methyl-[3-(1-methyl-2-pyrrolidinylmethyl) 1H-indol-5yl]methanesulfonamide (Alternative route)

(a) Methyl (N-diphenylmethyl-N-methylsulfamoyl)acetate

The subtitle compound (3.05 g, 37%) was prepared as a clear brown oil from N-methyl benzhydrylamine (prepared according to the method of Z. Horii, T Sakai and Inoi, *Pharm Bull.*, 1955, 3, 159) (10.7 g, 50.7 mmol) and methyl chlorosulfonylacetate (4.27 g, 24.7 mmol), using the method of Example 1(a).

$^1$H NMR (300 MHz, CDCl$_3$) δ=2.84 (3H, s), 3.72 (3H, s), 3.82 (2H, s), 6.43 (1H, s) 7.10–7.47(10H, m).

Found: C, 61.29; H 5.74; N, 4.21. C$_{17}$H$_{19}$O$_4$NS requires C, 61.24; H 5.74; N, 4.20%.

(b) (N-Diphenylmethyl-N-methylsulfamoyl)acetamide

The subtitle compound (2.62 g, 90%) was prepared as a white solid from aqueous ammonia solution (10 ml, s.g.= 0.88) and methyl (N-diphenylmethyl-N-methylsulfamoyl) acetate (from step (a), 3.05 g, 9.2 mmol), using the method of Example 1(b). m.p. 110–115° C.

$^1$H NMR (300 MHz, CDCl$_3$) δ=2.80 (3H, s), 3.72 (2H, s), 5.63 (1H, bs), 6.41 (1H, s), 6.60 (1H, bs), 7.05–7.48 (10H, m).

Found: C, 60.13; H 5.67; N, 8.75. C$_{16}$H$_{18}$N$_2$O$_3$S requires C, 60.36; H 5.77; N, 8.80%.

(c) 1-Cyano-N-diphenylmethyl-N-methylmethanesulfonamide

The subtitle compound (0.7 g, 71%) was prepared as a beige solid from (N-Diphenylmethyl-N-methylsulfamoyl) acetamide (from step (b), 1.0 g, 3.14 mmol) using the method of Example 1(c). m.p. 104–107° C.

$^1$H NMR (300 MHz, CDCl$_3$) δ=2.98 (3H, s), 3.71 (2H, s), 6.39 (1H, s), 7.20–7.46 (10H, m).

Found: C, 63.94; H, 5.38; N, 9.24. C$_{16}$H$_{16}$N$_2$O$_2$S requires C, 63.98; H, 5.37; N, 9.33%.

(d) 1-[(R)-1-Benzyl-3-(1-methyl-2-pyrrolidinylmethyl)-1H-indol-5-yl]-1-cyano-N-diphenylmethyl-N-methylmethanesulfonamide To a stirred solution of 1-cyano-N-diphenylmethyl-N-methylmethanesulfonamide (from step (c), 18.79 g, 62.6 mmol) in a mixture of toluene (60 ml) and ethylene glycol dimethylether (20 ml) at 0–5° C. under a nitrogen atmosphere was added sodium hydride (60% dispersion in mineral oil) (4.6 g, 115 mmol) portionwise, maintaining the temperature below 5° C. Upon completion of the addition, the dark brown solution was warmed to ambient temperature over a 30 min period, before tetrakis(triphenylphosphine) palladium(0) (3.61 g, 3.1 mmol) was added in one portion. A solution of (R)-1-benzyl-5-bromo-3-(1-methyl-2-pyrrolidinylmethyl)-1H-indole (from Example 1(d), 19.74 g, 52 mmol) in toluene (20 ml) was then added dropwise to the brown slurry and the mixture was warmed to reflux. Reflux was maintained for 2 hr after which time the dark brown solution was cooled to ambient temperature. The reaction mixture was then poured into water (250ml) and extracted with ethyl acetate (3×100 ml). The organic extracts were combined and evaporated in vacuo to yield a brown oil. This was re-dissolved in absolute ethanol (80 ml) and stirred for 18 hr over which time precipitation occurred. The solid seas filtered and dried in vacuo at 50° C. overnight to yield the subtitle compound (22 g, 70%) as a cream solid. m.p. 152–155° C.

$^1$H NMR (300 MHz, CDCl$_3$) δ=1.38–1.91 (4H, m), 2.14–2.30 (1H, m), 2.35–2.50 (4H, m), 2.55–2.70 (1H, m), 2.78 (3H, s), 3.02–3.20 (2H, m), 4.98 (1H, s), 5.28 (2H, s), 6.41 (1H, s), 6.89–7.53 (18H, m), 7.60 (1H, bs).

Found: C, 73.70; H, 6.28; N, 9.26. C$_{37}$H$_3$3 N4O$_2$S requires C, 73.72; H, 6.35; N, 9.29%.

(e) (R)-1-[1-Benzyl-3-(1-methyl-2-pyrrolidinylmethyl)-1H-indol-5-yl]-N-diphenylmethyl-N-methylmethanesulfonamide To a stirred solution of 1-[(R)-1-benzyl-3-(1-methyl-2-pyrrolidinylmethyl)-1H-indol-5-yl]-1-cyano-N-diphenylmethyl-N-methylmethanesulfonamide (from step (d), 11.61 g, 19.3 mmol) in ethanol (35 ml) at ambient temperature was added 2N potassium hydroxide solution (35 ml, 70 mmol). The dark brown solution was then brought to reflux and maintained at this temperature for 15 hr. The oily reaction mixture was then cooled to ambient temperature and extracted with ethyl acetate (3×100 ml). The organic extracts were combined and evaporated in vacuo to yield the crude product as a dark brown oil. The oil was diluted with ethanol (35 ml) and stirred at ambient temperature for 12 hr, which resulted in precipitation. The mixture was then filtered and the solid dried in vacuo at 50° C. overnight to yield the title compound (6.82 g, 61%) as a beige solid. m.p. 117–120° C.

¹H NMR (300 MHz, CDCl₃) δ=1.48–1.95 (4H, m), 2.16–2.32 (1H, m), 2.39–2.70 (8H, m), 3.05–3.25 (2H, m), 4.24 (2H, s), 5.26 (2H, s), 6.36 (1H, s) 6.90–7.49 (19H, m).

Found: C, 74.40; H, 6.75; N, 7.34. $C_{36}H_{39}N_3O_2S$ requires C, 74.80; H. 6.76; N, 7.27%. $[\alpha]_D$=+50.79 (c=1.8, $CH_2Cl_2$).

(f) (R)-N-Methyl-[3-(1-methyl-2-pyrrolidinylmethyl)-1H-indol-5-yl]methanesulfonamide

Into a stirred slurry of calcium tunings (1.11 g, 27.7 mmol) in tetrahydrofuran (1.2 ml) at −40° C. was added condensed liquid ammonia (16 ml). The blue bronze was stirred at −50 to −40° C. for a further 15 min, before a solution of (R)-1-[1-benzyl-3-(1-methyl-2-pyrrolidinylmethyl)-1H-indol-5-yl]-N-diphenylmethyl-N-methylmethanesulfonamide (from step (e), 4.0 g, 6.93 mmol) in tetrahydrofuran (10 ml) was added dropwise, maintaining the temperature below −40° C. The dark blue solution was stirred at −40° C. for a further 30 min, before saturated ammonium chloride solution (10 ml) was added dropwise and the grey solution warmed to ambient temperature. Water (10 ml) was then added and the white slurry stirred for 15 min, before being filtered in vacuo. The solid was then dissolved in 5N HCl (12 ml) and the resulting orange solution extracted with ethyl acetate (10 ml). The pH of the aqueous phase was then adjusted (pH=10) with 10N NaOH which resulted in precipitation. The solid was filtered and dried in vacuo at 50° C. overnight to yield the title compound (1.54 g, 73%) as a white solid. m.p. 209–212° C.

¹H NMR (300 MHz, DMSO) δ=1.36–1.81 (4H, m), 2.04–2.17 (1H, m), 2.28–2.52 (8H, m), 2.90–3.09 (2H, m), 4.34 (2H, s), 6.74–6.83 (1H, m), 7.07 (1H, d, J=9.7 Hz), 7.15 (1H, bs), 7.30 (1H, d, J=9.7 Hz), 7.51 (1H, s), 10.85 (1H, bs). LRMS (Thermospray): 322 (MH³⁰ ).

EXAMPLE 3

(R)-N-Methyl-[3-(1-methyl-2-pyrrolidinylmethyl)-1H-indol-5-yl]methanesulfonamide (Alternative route)

(a) (N-Methylsulfamoyl)acetamide

A solution of (N-benzyl-N-methylsulfamoyl)acetamide (see Example 1(b), 13.0 g, 50.5 mmol) in methanol (130 ml) was hydrogenated over Pearlman's catalyst (7.5 g) at 60° C. and at 345 kPa (50 psi) for 24 hr. The solution was then filtered through a pad of celite (trade mark) which was subsequently washed with acetone (50 ml). The combined filter was evaporated in vacuo to give a white solid which was dried in vacuo at 50° C. overnight to yield the subtitle compound (8.0 g, 98%) as a white solid. m.p. 104–108° C.

¹H NMR (250 MHz, DMSO) δ=2.55–2.65 (3H, d, J=4.9 Hz), 3.85 (2H, s), 6.88–7.05 (1H, m), 7.32 (1H, bs), 7.60 (1H, bs). LRMS (Thermospray) 169.7 ($MNH_4^+$).

(b)) 1-Cyano-N-methylmethanesulfonamide

The subtitle compound (0.87 g, 99%) was prepared as a beige solid from (N-methylsulfamoyl)acetamide (from step (a), 1.0 g, 6.57 mmol) by the method of Example 1(c). m.p. 36–39° C.

¹H NMR (300 MHz, DMSO) δ=2.65 (3H, s), 4.75 (2H, s), 7.85 (1H, bs). LRMS (Thermospray) 152.0 (MH⁺).

(c) N-Benzyloxymethy-1-cyano-N-methylmethanesulfonamide

To a stirred solution of 1-cyano-N-methylmethanesulfonamide (from step (b), 250 mg, 1.9 mmol) in tetrahydrofuran (5 ml) at 0–5° C. under an atmosphere of nitrogen was added sodium hydride (60% dispersion in mineral oil, 75 mg, 1.9 mmol) in one portion. The resulting slurry was stirred at 0–5° C. for 45 min, before benzyloxymethyl chloride (80% purity, 0.368 g, 1.9 mmol) in tetrahydrofuran (5 ml) was added dropwise over a 15 min period. The mixture was then allowed to warm to ambient temperature over a 3 hr period. The solvents were then evaporated in vacuo and the resulting oil was purified by flash column chromatography (diethyl ether:hexanes 3:1 as eluant) to yield the subtitle compound (296 mg, 61.6%) as a colourless oil.

$^1$H NMR (300 MHz, CDCl$_3$) δ=3.19 (3H, s), 4.05 (2H, s), 4.62 (2H, s), 4.81 (2H, s), 7.29–7.50 (5H, m). LRMS (Thermospray) 272.3 (MNH$_4$$^+$).

(d) (R)-1-Benzyloxnmethyl-5-bromo-3-(1-methyl-2-pyrrolidinylmethyl)-1H-indole To a stirred suspension of potassium tert-butoxide (5.5 g, 45 mmol) in tetrahydrofuran (30 ml) at 0–5° C. under a nitrogen atmosphere was added a solution of (R)-5-bromo-3(1-methyl-2-pyrrolidinylmethyl)-1H-indole (12 g, 41 mmol) in THF (40 ml) dropwise, maintaining the temperature below 10° C. Upon completion of the addition, the dark brown solution was stirred at 0–5° C. for 1 hr before benzylchloromethylether (80% purity, 8.8 g, 45 mmol) was added dropwise maintaining the temperature below 5° C. The brown solution was then warmed to ambient temperature over a 1 hr period before being quenched into water (100 ml). The mixture was then extracted with ethyl acetate (3×25 ml) and the combined organic phases were evaporated in vacuo to yield a brown oil. This was purified by flash column chromatography (ethyl acetate:triethylamine 100:5 as eluant) to give the subtitle compound (14.1 g, 83%) as a brown oil.

$^1$H NMR (300 MHz, CDCl$_3$) δ=1.42–1.95 (4H, m), 2.11–2.32 (1H, m), 2.32–2.65 (5H, m), 3.0–3.20 (2H, m), 4.36 (2H, s), 5.48 (2H, s), 7.01 (1H, s), 7.13–7.42 (7H, m), 7.72 (1H, s). LRMS (Thermospray): 413.3 (MH$^+$)

(e) N-Benzyloxymetyl-1-[(R)-1-benzyloxymethyl-3-(1-methyl-2-pyrrolidinalmethy)-1H-indol-5-yl]-1-cyano-N-methylmethanesulfonamide

To a stirred suspension of sodium hydride (60% dispersion in mineral oil, 470 mg, 11.7 mmol) and tetrakis (triphenylphosphine) palladium(0) (370 mg, 0.32 mmol) in a mixture of toluene (5 ml) and ethylene glycol dimethylether (1.62 ml) under a nitrogen atmosphere was added a solution of N-benzyloxymethyl-1-cyano-N-methylmethanesulfonamide (from step (c), 1.62 g, 6.4 mmol) in toluene (2.2 ml) at 0–5° C. The mixture was then warmed to ambient temperature and stirred for 30 min, before a solution of (R)-1-benzyloxymethyl-5-bromo-3-(1-methyl-2-pyrrolidinylmethyl)-1H-indole (from step (d), 2.2 g, 5.3 mmol) in toluene (2.2 ml) was added in one portion and the mixture was warmed to reflux. Reflux was maintained for 2 hr after which time the dark brown solution was cooled to ambient temperature. The reaction mixture was then poured into water (20 ml) and extracted with ethyl acetate (3×15 ml). The organic extracts were combined and evaporated in vacuo to yield a brown oil. This was purified by flash column chromatography (ethyl acetate:triethylamine 97.5:2.5) to give the subtitle compound (2.98 g, 95%) as a brown oil.

$^1$H NMR (300 MHz, CDCl$_3$) δ=1.46–1.95 (4H, m), 2.15–2.30 (1H, m), 2.37–2.75 (5H, m), 3.02 (3H, s), 3.05–3.20 (2H, m), 4.40 (3H, s), 4.47–4.62 (4H, m), 5.31 (1H, s), 5.50 (2H, s), 7.08 (1H, s), 7.20–7.81 (13H, m). LRMS (Thermospray): 586.7 (MH$^+$).

(f) (R)-N-Benzyloxymethyl-1-[1-benzyloxymethyl-3-(1-methyl-2-pyrrolidinylmethyl)-1H-indol-5-yl]-N-methylmethanesulfonamide

17

To a stirred solution of N-benzyloxymethyl-1-[(R)-1-benzyloxymethyl-3-(1-methyl-2-pyrrolidinylmethyl)-1H-indol-5-yl]-1-cyano-N-methylmethanesulfonamide (from step (e), 2.0 g, 3.4 mmol) in IMS (14 ml) at ambient temperature was added 2N potassium hydrodroxide solution (7 ml, 14 mmol). The dark brown solution was then brought to reflux and maintained at this temperature for 15 hr. The oily reaction mixture was then cooled to ambient temperature and extracted with ethyl acetate (3×20 ml). The organic extracts were combined and evaporated in vacuo to yield a dark brown oil. This was purified by flash column chromatography (ethyl acetate:triethylamine 95:5 as eluant) to yield the subtitle compound (631 mg, 33%) as a brown oil.

$^1$H NMR (300 MHz, CDCl$_3$) 1.46–1.94 (4H, m), 2.16–2.32 (1H, m), 2.37–2.75 (5H, m), 2.89 (3H, s), 3.05–3.23 (2H, m), 4.3–4.52 (10H, m), 5.51 (2H, s), 6.93–7.66 (14H, m). LRMS (Thermospray): 562.5 (MH$^+$).

(g) (R)-N-Methyl-[3-(1-methyl-2-pyrrolidinylmethyl)-1H-indol-5-yl]methanesulfonamide A mixture of (R)-N-Benzyloxymethyl-1-[1-benzyloxymethyl-3-(1-methyl-2-pyrrolidinylmethyl)-1H-indol-5-yl]-N-methylmethanesulfonamide (from step (f), 300 mg, 0.5 mmol) and methanesulfonic acid (60 mg, 0.6 mmol) in water (5 ml) was hydrogenated over Pearlman's catalyst (300 mg) at 60° C. and at 345 kPa (50 psi) for 18 hr. The solution was then filtered through a pad of celite (trade mark) and the filtrate was partitioned between saturated sodium bicarbonate (25 ml) and dichloromethane (3×50 ml). The combined organic extract was then evaporated in vacuo and the residue was dissolved in a mixture of THF and water (1:1) (10 ml). A solution of Triton B (40% w.w. in methanol) (0.2 ml, 0.44 mmol) was then added dropwise and the solution was then refluxed for 2 hr. The solution was then cooled to ambient temperature before being poured into water (10 ml) and extracted with dichlo-

18 romethane (3×25 ml). The combined organic extracts were evaporated in vacuo to give a yellow film. This was then triturated with IMS (5 ml) and tie solid was filtered in vacuo and dried at 50° C. overnight to yield the title compound (50 mg, 29%) as a white solid. m.p. 209–231° C.

$^1$H NMR (300 MHz DMSO) δ=1.36–1.81 (4H, m), 2.04–2.17 (1H,m), 2.28–2.52 (8H, m), 2.90–3.09 (2H, m), 4.34 (2H, s), 6.74–6.83 (1H, m), 7.07 (1H, d, J=9.7 Hz), 7.15 (1H, bs), 7.30 (1H, d, J=9.7 Hz), 7.51 (1H, s), 10.85 (1H, bs). LRMS (Thermospray): 322 (MH$^+$).

EXAMPLE 4

(R)-N-Benzyl-N-methyl-1-[3-(1-methyl-2-pyrrolidinylmethyl)-1-trimethysilyethyloxmethyl-1H-indol-5-yl]methanesulfonamide

(a) (R)-5-Bromo-3-1-methyl-2-pyrrolidinylmethyl)-1-trimethsilylethyloxymethyl -1H-indole To a stirred solution of (R)-5-bromo-3-(1-methyl-2-pyrrolidinylmethyl)-1H-indole (10 g, 34.1mmol) in tetrahydrofuran (100 ml) at 0° C. under a nitrogen atmosphere was added sodium hydride (60% dispersion in mineral oil) (1.5 g, 37.5 mmol) portionwise, maintaining the temperature below 5° C. Upon completion of the addition, the dark brown solution was stirred at 0–5° C. for 10 min before trimethylsilylethyloxymethyl chloride (6.64 ml, 37.5 mmol) was added dropwise maintaining the temperature below 5° C. The brown solution was then warmed to ambient temperature over a 1 hr period before being quenched into water (100 ml). The mixture was then extracted with ethyl acetate (3×25 ml) and the combined organic extracts were evaporated in vacuo to yield a brown oil. This was purified by flash column chromatography (ethyl acetate:hexane 1:1 as eluant) to yield the subtitle compound (8.96 g, 62%) as a brown oil.

$^1$H NMR (300 MHz, CDCl$_3$) δ=0.95 (9H, s), 0.89 (2H, t, J=6.8 Hz), 1.42–1.86 (4H, m), 2.14–2.30 (1H, m), 2.35–2.60 (5H, m), 3.05–3.18 (2H, m), 3.42 (2H, t, J=6.8 Hz), 5.41 (2H, s), 7.31 (2H, s), 7.71 (1H, s). LRMS (Thermospray): 424.5 (MH$^+$).

(b) N-Benzyl-1-cyano-N-methyl-1-[(R)-3-(1-methyl-2-pyrrolidinylmethyl-1-trimethylsilylethyloxethyl-1H-indol-5-yl]methanesulfonamide To a stirred slurry of N-benzyl-1-cyano-N-methylmethanesulfonamide (from step (a), 1.42 g, 6.33 mmol) and tetrakis(triphenylphosphine) palladium(0) (399 mg, 0.34 mmol) in ethylene glycol dimethylether (5 ml)) at 0° C. under a nitrogen atmosphere was added sodium hydride (60% dispersion in mineral oil) (495 mg, 12.4 mmol) portion wise, maintaining the temperature below 5° C. The brown solution was then warned to ambient temperature over a 10 minute period, before a solution of (R)-5-bromo-3-(1-methyl-2-pyrrolidinylmethyl)-1-trimethylsilylethyloxymethyl-1H-indole (see Example 1(c), 2.44 g, 5.8 mmol) in toluene (20 ml) was added dropwise and the mixture was then warmed to reflux. Reflux was maintained for 1.5 hr after which time the dark brown solution was cooled to ambient temperature. The reaction mixture was then poured into water (50 ml) and extracted with ethyl acetate (3×25 ml). The organic extracts were combined and evaporated in vacuo to yield a brown oil. This was purified by flash column chromatography (ethyl acetate-:hexane:diethylamine 1:1:0.1 as eluant) to yield the subtitle compound (3.25 g, 99%) as a brown oil.

$^1$H NMR (300 MHz, CDCl$_3$) δ=0.93 (9H, s), 0.88 (2H, t, J=6.8 Hz), 1.46–1.90 (4H, m), 2.15–2.30 (1H, m), 2.44 (3H, s), 2.60–2.76 (4H, m), 3.05–3.20 (2H, m), 3.45 (2H, t, J=6.8 Hz), 4.20 (2H, s), 5.28, (1H, s), 5.45 (2H, s), 7.10 (1H, s), 7.22–7.43 (6H, m), 7.50–7.58 (1H, s), 7.78 (1H, s). LRMS (Thermospray): 567 (MH$^+$).

(c) (R)-N-Benzyl-N-methyl-1-[3-(1-methyl-2-pyrrolidinylmethyl)-1-trimethylsilylethyloxymethyl-1H-indol-5-yl]methanesulfonamide

To a stirred solution of N-benzyl-1-cyano-N-methyl-1-[(R)-3-(1-methyl-2-pyrrolidinylmethyl)-1-trimethylsilylethyloxymethyl-1H-indol-5-yl]methanesulfonamide (from step (b), 1.56 g, 2.8 mmol) in ethanol (12 ml) at ambient temperature was added 2N potassium hydroxide solution (6.24 ml, 12.5 mmol). The dark brown solution was then brought to reflux and maintained at this temperature for 15 hr. The oily reaction mixture was then cooled to ambient temperature and extracted with ethyl acetate (3×25 ml). The organic extracts were combined and evaporated in vacuo to yield the crude product as a dark brown oil. This was purified by flash column chromatography (ethyl acetate:hexane:dietiylamine 1:1:0.1 as eluant) to yield the title compound (1.49 g, 75%) as a brown oil.

$^1$H NMR (300 MHz, CDCl$_3$) δ=0.91 (9H, s), 0.85 (2H, t, J=6.8 Hz), 1.48–1.88 (4H, m), 2.15–2.30 (1H, m), 2.36–2.69 (8H, m), 3.05–3.20 (2H, m), 3.45 (2H, t, J=6.8 Hz), 4.20 (2H, s), 4.42 (2H, s), 5.42 (2H, s), 7.08 (1H, s), 7.14–7.34 (6H, m), 7.40–7.55 (1H, d), 7.56 (1H, s). LRMS (Thermospray): 542.8 (MH$^+$).

EXAMPLE 5

(R)-1-[1-Allyl-3-(1-methyl-2-pyrrolidinylmethyl-1H-indol-5yl]-N-diphenylmethyl-N-methylmethanesulfonamide (a) (R)-1-Allyl-5-bromo-3-(1-methyl-2-pyrrolidinylmethyl)-1H-indole To a stirred solution of (R)-5-bromo-3-(1-methyl-2-pyrrolidinylmethyl)-1H-indole (22.5 g, 76.8 mmol) in tetrahydrofuran (132 ml) at 0° C. under a nitrogen atmosphere was added potassium tert-butoxide (9.47 g, 84.4 mmol) portionwise, maintaining the temperature below 5° C. Upon completion of the addition, the dark brown slurry was stirred at 0–5° C. for 30 min before allyl bromide (7.3 ml, 84.3 mmol) was added dropwise maintaining the temperature below 5° C. The brown solution was then warmed to ambient temperature over a 1 hr period before being quenched into water (100 ml). The mixture was then extracted with ethyl acetate (3×25 ml) and the combined organic extracts were evaporated in vacuo to give a brown oil. This was purified by flash column chromatography (ethyl acetate:hexane:diethylamine 1:1:0.1 as eluant) to yield the subtitle compound (19.94 g, 78%) as a golden oil.

$^1$H NMR (300 MHz, CDCl$_3$) δ=1.42–1.92 (4H, m), 2.15–2.35 (1H, m), 2.38–2.64 (5H, m), 3.02–3.22 (2H, m), 4.66 (2H, d, J=4.8 Hz), 4.98–5.25 (2H, m), 5.88–6.14 (1H, m), 6.39 (1H, s), 7.15 (1H, d, J9.7 Hz), 7.25 (1H, d, J=9.7 Hz), 7.72 (1H, s). LRMS (Thermospray): 333 (MH$^+$). [α]$_D$ +62.90° (c=6, CH$_2$Cl$_2$).

(b) 1-[(R)-1-Allyl-3-(1-methyl-2-pyrrolidinylmethyl)-1H-indol-5-yl]-1-cyano-N-diphenylmethyl-N-methylmethanesulfonamide To a stirred solution of 1-cyano-N-diphenylmethyl-N-methylmethanesulfonamide (see Example 2(c), 1.36 g, 4.5 mmol) in toluene (5 ml) at 0° C. under a nitrogen atmosphere was added sodium hydride (60% dispersion in mineral oil) (345 mg, 8.6 mmol) portionwise, maintaining the temperature below 5° C. The dark brown solution was then warmed to ambient temperature over a 30 min period, before tetrakis(triphenylphosphine) palladium(0) (285 mg, 0.25 mmol) was added in one portion. A solution of (R)-1-allyl-5-bromo-3-(1-methyl-2-pyrrolidinylmethyl)-1H-indole (from step (a), 1.37 g, 4.1 mmol) in toluene (5 ml) was then added dropwise to the yellow/green slurry and the mixture was warmed to reflux. Reflux was maintained for 2 hr after which time the dark brown solution was cooled to ambient temperature. The reaction mixture was then poured into water (50 ml) and extracted with ethyl acetate (3×25 ml). The organic extracts were combined and evaporated in vacuo to yield a brown oil. This was purified by flash column chromatography (ethyl acetate:hexane:diethylamine 1:1:0.1 as eluant) to yield the subtitle compound (1.81 g, 80%) as a brown oil.

$^1$H NMR (300 MHz, CDCl$_3$) δ=1.42–1.95 (4H, m), 2.16–2.30 (1H, m), 2.35–2.66 (4H, m), 2.75 (3H, s), 3.02–3.20 (2H, m), 4.66 (2H, d, J=4.8 Hz), 4.95–5.15 (3H, m), 5.16–5.25 (1H, m), 5.86–6.06 (1H, m), 6.43 (1H, s), 6.98 (1H, s), 7.10–7.50 (12H, m), 7.58 (1H, m). LRMS (Thermospray): 552.7 (MH$^+$).

(c) (R)-1-[1-Allyl-3-(1-methyl-2-pyrrolidinylmethyl)-1H-indol-5-yl]-N-diphenylmethyl-N-methylmethanesulfonamide

To a stirred solution of 1-[(R)-1-allyl-3-(1-methyl-2-pyrrolidinylmethyl)-1H-indol-5-yl]-1-cyano-N-diphenylmethyl-N-methylmethanesulfonamide (from step (b), 5.11 g, 9.25 mmol) in ethanol (10.22 ml) at ambient temperature was added 2N potassium hydroxide solution (20.4 ml, 41 mmmol). The dark brown solution was then brought to reflux and maintained at this temperature for 15 hr. The oily reaction mixture was then cooled to ambient temperature and extracted with ethyl acetate (3×50 ml). The organic extracts were combined and evaporated in vacuo to yield a dark brown oil. This was purified by flash column chromatography (ethyl acetate:hexane:diethylamine 1:1:0.1 as eluant) to yield the title compound (3.7 g, 76%) as a brown oil.

$^1$H NMR (300 MHz, CDCl$_3$) δ=1.42–1.93 (4H, m), 2.14–2.29 (1H, m), 2.34–2.73 (8H, m), 3.01–3.20 (2H, m), 4.27 (2H, s), 4.66 (2H, d, J=4.8 Hz), 4.96–5.28 (2H, m), 5.88–6.06 )1H, m), 6.38 (1H, s), 6.88–7.44 (14H, m). LRMS (Thermospray): 528.9 (MH$^+$) [α]$_D$ +52.7° (c=0.88, CH$_2$Cl$_2$).

EXAMPLE 6

N-tert-Butyl-1-cyano-N-methyl-1-[(R)-3(1-methyl-2-pyrrolidinylmethyl)-1-tosyl-1H -indol-5-yl] methanesulfonamide (a) Methyl(N-tert-butyl-N-methylsulfamoyl)acetate The subtitle compound (14.81 g, 59%) was prepared as a yellow oil from tert-butylmethylamine (24.48 g, 0.28 mol) and methyl chlorosulfonylacetate (19.37 g, 0.11 mmol), using the method of Example 1(a).

$^1$H NMR (300 MHz, CDCl$_3$) δ=1.42 (9H, s), 2.90 (3H, s), 3.77 (3H, s), 3.97 (2H, s).

Found: C, 43.21; H, 7.71; N, 6.31. C$_8$H$_{17}$NO$_4$S requires C, 43.03; H, 7.67; N, 6.27%.

(b) (N-tert-Butyl-N-methylsulfamoyl)acetamide

The subtitle compound (3.66 g, 84%) was prepared as a white solid from aqueous ammonia solution (10 ml, s.g.= 0.88) and methyl (N-tert-butyl-N-methylsulfamoyl)acetate (from step (a), 4.7 g, 21 mmol), using the method of Example 1(b). m.p. 105–109° C.

$^1$H NMR (300 MHz, CDCl$_3$) δ=1.47 (9H, s), 2.95 (3H, s), 3.90 (2H, s), 5.50 (1H, bs), 6.63 (1H, bs).

Found: C, 40.31; H, 7.70; N, 13.41. C$_7$H$_{16}$N$_2$O$_3$S requires C, 40.37; H, 7.74; N, 13.45%.

(c) N-tert-Butyl-1-cyano-N-methylmethanesulfonamide

The subtitle compound (7.31 g, 96%) was prepared as a yellow oil from (N-tert-butyl-N-methylsulfamoyl)acetamide (from step (b), 8.31 g, 40 mmol) using the method of Example 1(c).

$^1$H NMR (300 MHz, CDCl$_3$) δ=1.49 (9H, s), 3.07 (3H, s), 3.97 (2H, s).

Found: C, 44.20; H 7.51; N, 14.70. C$_7$H$_{14}$N$_2$O$_2$S requires C, 44.19; H 7.42; N, 14.72%.

(d) (R)-5-Bromo-3-(1-methyl-2-pyrrolidinylmethyl)-1-tosyl-1H-indole

To a stirred solution of (R)-5-bromo-3-(1-methyl-2-pyrrolidinylmethyl)-1H-indole (10.0 g, 34.1 mmol) in ethyleneglycol dimethylether (50 ml) at 0° C. under a nitrogen atmosphere was added potassium hydroxide flake (9.58 g, 171 mmol) in one portion. Para-toluenesulfonyl chloride (6.83 g, 35.8 mmol) was then added portionwise to the brown slurry over a 5 min period, maintaining the temperature below 5° C. The brown slurry was then warmed to ambient temperature and stirred for a further 2 hr. The mixture was then filtered in vacuo and the filter cake washed with toluene (2×100 ml). The filtrate was then concentrated in vacuo to approximately 20 ml volume which resulted in precipitation of a cream solid. After stirring for 2 hr, the solid was filtered and dried in vacuo at 50° C. for 12 hr to give the title compound (9.91 g, 65%) as a beige solid. m.p. 98–104° C.

$^1$H NMR (300 MHz, CDCl$_3$) δ=1.54–1.84 (4H, m), 2.15–2.28 (1H, m), 2.30–2.58 (8H, m), 2.90–3.15 (2H, m), 7.15–7.30 (2H, m), 7.35–7.42 (2H, m), 7.58 (1H, m), 7.65–7.9 (3H, m). LRMS (Thermospray) 449.4 (MH$^+$). [α]$_D$ +52.9° (c=5.1, CH$_2$Cl$_2$).

(e) N-tert-Butyl-1-cyano-N-methyl-1-[(R)-3-(1-methyl-2-pyrrolidinylmethyl)-1-tosyl-1H-indol-5-yl]methanesulfonamide To a stirred suspension of dichlorobis (triphenylphosphine)palladium (II) (704 mg, 1 mmol) and triphenylphosphine (525 mg, 2 mmol) in ethyleneglycol dimethylether (5 ml) at ambient temperature under an atmosphere of nitrogen was added sodium borohydride (38 mg, 1 mmol) in one portion. The green slurry was stirred for 5 min, then N-tert-butyl-cyano-N-methylmethanesulfonamide (from step (c), 1.04 g, 5.4 mmol) was added in one portion. The green slurry was then cooled to 0–5° C. and sodium hydride (60% dispersion in mineral oil) (441 mg, 11 mmol) was added portionwise, maintaining the temperature below 5° C. The brown solution was then warmed to ambient temperature over a 10 min period, before a solution of (R)-5-bromo-3-(1-methyl-2-pyrrolidinylmethyl)-1-tosyl-1H-indole (from step (d), 2.24 g, 5 mmol) in ethyleneglycol dimethyl ether (15 ml) was added dropwise. The brown slurry was then warmed to reflux. Reflux was maintained for 1.5 hr after which time the dark brown solution was cooled to ambient temperature. The reaction mixture was then poured into water (20 ml) and extracted with ethyl acetate (3×25 ml). The organic extracts were combined and evaporated in vacuo to yield a brown oil. This was purified by flash column chromatography (ethyl acetate:hexane:diethylamine 1:1:0.1 as eluant) to yield the subtitle compound (1.23 g, 45%) as a golden oil.

$^1$H NMR (300 MHz, CDCl$_3$) δ=1.44 (9H, s), 1.54–1.84 (4H, m), 2.15–2.28 (1H, m), 2.32–2.66 (8H, m), 2.85 (3H, s), 2.95–3.15 (2H, m), 5.15 (1H, s), 7.18–7.28 (2H, m), 7.39–7.50 (2H, m), 7.62–7.76 (3H, m), 7.96–8.05 (1H, s). LRMS (Thermospray): 557.8 (MH$^+$).

EXAMPLE 7

3-[2-(Dimethylamino)ethyl]-N-methy-1H-indole-5-methanesulfonamide (a) 5-bromo-N,N-dimethyl-α-oxo-1H-indole-3-acetamide To a solution of 5-bromoindole (15.85 g, 81 mmol) in tetrahydrofuran (80 ml) at 0–5° C. under an atmosphere of nitrogen was added oxalyl chloride (7.76 ml 89 mmol) dropwise, maintaining the temperature below 5° C. The cloudy solution was then warmed to ambient temperature and stirred for 30 min, before being re-cooled to 0–5° C. The solution was then saturated with anhydrous dimethylamine for 30 min, which resulted in formation of a yellow precipitate. The slurry was then warmed to ambient temperature and diluted with demineralised water (100 ml) before being extracted with dichloromethane (3×50 ml). The organic extracts were combined and evaporated in vacuo to give a white solid. This was slurried in a mixture of ethyl acetate-:hexane (1:1) (40 ml) for 8 hr and then filtered in vacuo to give the subtitle compound (20.28 g, 85%) as a white solid. m.p. 189–190° C.

$^1$H NMR (300 MHz, CDCl$_3$) δ=2.90 (3H, s), 2.96 (3H, s), 7.35–7.55 (2H, m), 8.15 (1H, s), 8.22 (1H, d, J=0.97 Hz).

Found: C, 48.71; H, 3.72; N, 9.41. Cl$_{12}$H$_{11}$BrN$_2$O$_2$ requires C, 48.84; H, 3.76; N, 9.49%.

(b) 5-Bromo-3-[2-(dimethylamino)ethyl]-1H-indole

A solution of 5-bromo-N,N-dimethyl-α-oxo-1H-indole-3-acetamide (from step (a), 19.85 g, 67.3 mmol) in tetrahydrofuran (100 ml) was added dropwise to a slurry of lithium aluminium hydride (7.66 g, 0.2 mol) in tetrahydrofuran (20 ml) under a nitrogen atmosphere, maintaining the temperature below 5° C. The yellow green slurry was then warmed to ambient temperature and then brought to gentle reflux. Reflux was maintained for 5 hr after which time the reaction mixture was cooled to 0° C. and isopropyl alcohol (150 ml) and IMS (150 ml) were added sequentially. The grey slurry was then warmed to ambient temperature, before 1N NaOH (100 ml) was added. The reaction mixture was then filtered through a celite (trade mark) pad and the pad washed consecutively with demineralised water (100 ml) and IMS (100 ml). The filtrate was then concentrated under reduced pressure until all alcohol had been removed and then the aqueous residue was extracted with ethyl acetate (2×200 ml). The combined organic extracts were then evaporated in vacuo to give a brown oil. This was triturated with a mixture of hexane and ethyl acetate (1:1) (30 ml) to give the subtitle compound (13.4 g, 75%) as a cream solid. m.p. 82–85° C.

$^1$H NMR (300 MHz, CDCl$_3$) δ=2.34 (6H, s), 2.62 (2H, t, J=7.8 Hz), 2.90 (2H, t, J=7.8 Hz), 7.0, (1H, s), 7.1–7.35 (2H, m), 7.72 (1H, s), 8.26 (1H, bs).

Found: C, 53.94; H, 5.61; N, 10.40. C$_{12}$H$_{15}$BrN$_2$ requires C, 53.95; H, 5.66; N, 10.49%.

(c) 1-Benzyl-5-bromo-3-[2-(dimethylamino)ethyl]-1H-indole

-continued

To a stirred solution of 1-Benzyl-5-bromo-3-[2-(dimethylamino)ethyl]-1H-indole (from step (b), 10.18 g, 38.1 mmol) in tetrahydrofuran (50 ml) at 0° C. under a nitrogen atmosphere was added sodium hydride (60% dispersion in mineral oil) (1.68 g, 42 mmol) portionwise, maintaining the temperature below 5° C. Upon completion of the addition, the dark brown solution was stirred at 0–5° C. for 1 hr before benzyl bromide (4.99 ml, 42 mmol) was added dropwise maintaining the temperature below 5° C. The brown solution was then warmed to ambient temperature over a 1 hr period before being quenched into water (100 ml). The mixture was then extracted with ethyl acetate (3×25 ml) and the organic extracts were combined and evaporated in vacuo to yield a brown oil. This was purified by flash column chromatography (ethyl acetate:hexane:diethylamine 1:1:0.1 as eluant) to give the subtitle compound (7.07 g, 52%) as a white solid. m.p. 49–50° C.

$^1$H NMR (300 MHz, CDCl$_3$) δ=2.34 (6H, s), 2.60 (2H, t, J=7.8 Hz), 2.89 (2H, t, J=7.8 Hz), 5.23 (2H, s), 6.95, (1H, s), 7.01–7.40 (7H, m), 7.72 (1H, m).

Found: C, 63.69; H, 5.93; N, 7.76. C$_{19}$H$_{21}$BrN$_2$ requires C, 63.87; H,5.92; N, 7.84%.

(d) 1-[1-Benzyl-3-[2-(dimethylamino)ethyl]-1H-indol-5-yl]-1-cyano-N-diphenylmethyl-N-methylmethanesulfonamide

To a stirred solution of 1-cyano-N-diphenylmethyl-N-methylmethanesulfonamide (see Example 2(c), 2.36 g, 7.9 mmol) in a mixture of toluene (4 ml) and ethylene glycol dimethylether (1 ml) at 0–5° C. under a nitrogen atmosphere was added sodium hydride (60% dispersion in mineral oil) (577 mg, 14.4 mmol) portionwise, maintaining the temperature below 5° C. Upon completion of the addition, the dark brown solution was warmed to ambient temperature over a 30 min period, before tetrakis(triphenylphospline) palladium(0) (529 g, 0.46 mmol) was added in one portion. A solution of 1-benzyl-5-bromo-3-[2-(dimethylamino) ethyl]-1H-indole (from step (c), 2.34 g, 6.6 mmol) in toluene (2 ml) was then added dropwise to the brown slurry and the mixture was warmed to reflux. Reflux was maintained for 2 hr after which time the dark brown solution was cooled to ambient temperature. The reaction mixture was then poured into water (25 ml) and extracted with ethyl acetate (3×5 ml). The organic extracts were combined and evaporated in vacuo to yield a brown oil. This was re-dissolved in absolute ethanol (8 ml) and stirred for 18 hr over which time precipitation occurred. The solid was filtered and dried in vacuo at 50° C. overnight to yield the subtitle compound (1.3 g, 35%) as a cream solid. m.p. 98–100° C.

$^1$H NMR (300 MHz, CDCl$_3$) δ=2.30 (6H, s), 2.52 (2H, m), 2.75 (3H, s), 2.80–2.92 (2H, m), 4.96 (1H, s), 5.24 (2H, s), 6.39 (1H, s), 6.94–7.75 (19H, m).

Found: C, 72.56; H, 6.29; N, 9.31. C$_{35}$H$_{36}$N$_4$O$_2$S requires C, 72.89; H, 6.29; N, 9.71%.

(e) 1-[1-Benzyl-3-[2-(dimethylamino)ethyl]-1H-indol-5-yl]-N-diphentlmethyl-N-methylmethanesulfonamide To a stirred solution of 1-[1-benzyl-3-[2-(dimethylamino) ethyl]-1H-indol-5-yl]-1-cyano-N-diphenylmethyl-N-methylmethanesulfonarmide (from step (d), 3.01 g, 5.2 mmol) in IMS (15 ml) at ambient temperature was added 2N potassium hydroxide solution (15 ml, 30 mmol). The dark brown solution was then brought to reflux and maintained at this temperature for 15 hr. The oily reaction mixture was then cooled to ambient temperature and extracted with ethyl acetate (3×100 ml). The organic extracts were combined arid evaporated in vacuo to yield the crude product as a dark brown oil. This was purified by flash column chromatography (ethyl acetate:hexane:diethylamine 1:1:0.1 as eluant) to yield the subtitle compound (2.14 g, 74%) as a pale yellow solid. m.p. 98–100° C.

$^1$H NMR (300 MHz, CDCl$_3$) δ=2.35 (6H, s), 2.54–2.65 (5H, m), 2.85 (2H, t, J=8.7 Hz), 4.27 (2H, s), 5.24 (2H, s), 6.35 (1H, s), 6.94–7.43 (19H, m).

Found: C, 74.47; H, 6.44; N, 7.79. $C_{34}H_{37}N_3O_2S$ requires C, 74.01; H, 6.76; N, 7.62%.

(f) 3-[2-(Dimethylamino)ethyl]-N-methyl-1H-indole-5-methanesulfonamide

To a stirred slurry of calcium turnings (243 mg, 6 mmol) in tetrahydrofuran (4 ml) at −40° C. was condensed liquid ammonia (4 ml). The blue bronze was stirred at −50 to −40° C. for a further 15 min, before a solution of 1-[1-benzyl-3-[2-(dimethylamino)ethyl]-1H-indol-5-yl]-N-diphenylmethyl-N-methylmethanesulfonamide (from step (e), 836 mg, 1.5 mmol) in tetrahydrofuran (2 ml) was added dropwise, maintaining the temperature below −40° C. The dark blue solution was stirred at −40° C. for a further 30 minutes, before saturated ammonium chloride solution (10 ml) was added dropwise and the grey solution warmed to ambient temperature. Water (10 ml) was then added and the white slurry stirred for 15 min, before being filtered in vacuo. The solid was then dissolved in 5N HCl (12 ml) and the resulting orange solution extracted with ethyl acetate (10 ml). The pH of the aqueous phase was then adjusted (pH=10) with 10N NaOH which resulted in precipitation. The solid was filtered and dried in vacuo at 50° C. overnight to yield the title compound (250 mg, 56%) as a white solid. m.p. 159–163° C.

$^1$H NMR (300 MHz, CDCl$_3$) δ=2.22 (6H, s), 2.53–2.61 (5H, m), 2.75–2.89 (2H, m)4.33 (2H, s), 6.75 (1H, q, J=3 Hz), 7.05 (1H, d, J=4.85 Hz), 7.15 (1H, s), 7.30 (1H, d, J=Hz), 7.50 (1H, s), 10.8 (1H, bs). LRMS (thermospray) 296.4 (MH$^+$)

What is claimed is:

1. A compound of formula I wherein $R^1$ and $R^2$ independently represent N-protecting groups stable to basic hydrolysis conditions and removable by hydrogenolysis; and $R^3$ represents a $C_{1-6}$ alkyl group substituted by:

(i) a 5- or 6-membered nitrogen-containing saturated heterocyclic group which in turn may be substituted by $C_{1-6}$ alkyl or a pyrimidine ring which is itself substituted by $C_{1-6}$ alkoxy; or

(ii) di($C_{1-6}$ alkyl)amino.

2. A compound of formula III wherein $R^1$ is an N-protecting group stable to basic hydrolysis conditions and removable by hydrogenolysis.

3. A compound of formula IV wherein $R^1$ and $R^2$ independently represent N-protecting groups stable to basic hydrolysis conditions and removable by hydrogenolysis; and $R^3$ represents a $C_{1-6}$ alkyl group substituted by:

(i) a 5- or 6-membered nitrogen-containing saturated heterocyclic group which in turn may be substituted by $C_{1-6}$ alkyl or a pyrimidine ring which is itself substituted by $C_{1-6}$ alkoxy; or (ii) di($C_{1-6}$ alkyl)amino.

4. A process for the production of a compound of formula I, wherein $R^1$ and $R^2$ independently represent N-protecting groups stable to basic hydrolysis conditions and removable by hydrogenolysis; and $R^3$ represents a $C_{1-6}$ alkyl group substituted by:

(i) a 5- or 6-membered nitrogen-containing saturated heterocyclic group which in turn may be substituted by $C_{1-6}$ alkyl or a pyrimidine ring which is itself substituted by $C_{1-6}$ alkoxy; or (ii) di($C_{1-6}$ alkyl)amino;

which comprises reacting a compound of formula II, wherein Hal represents Cl, Br or I; and $R^2$ and $R^3$ are as defined above; with a compound of formula III, wherein $R^1$ is as defined above;
in the presence of a strong base and a palladium(0) catalyst, at an elevated temperature, in a solvent which does not adversely affect the reaction.

5. A process as claimed in claim 4, wherein the strong base is sodium hydride or potassium t-butoxide.

6. A process according to claim 4, wherein the palladium (0) catalyst is tetrakis(triphenylphosphine)palladium(0).

7. A process according to claim 4, wherein the solvent is a mixture of toluene and ethylene glycol-dimethylether.

8. A process as claimed in claim 4, wherein Hal is Br.

9. A process for the production of a compound of formula V, wherein
$R^3$ is as defined in claim 4;
which comprises:
(i) basic hydrolysis of the cyano group of a compound of formula I as defined in claim 1, followed by decar- boxylation of the resulting carboxylic acid, to provide a compound of formula IV, wherein $R^{1-3}$ are as defined in claim 4; followed by (ii) replacement of $R^1$ and $R^2$ with H.

10. A process as claimed in claim 9, wherein step (i) is carried out using aqueous potassium hydroxide in ethanol at an elevated temperature.

11. A process according to claim 9, wherein step (ii) is carried out using hydrogenolysis.

12. A process according to claim 4 or claim 9, wherein $R^1$ represents benzyl, $CH_2OCH_2(C_6H_5)$, $CH(C_6H_5)_2$ or t-butyl.

13. A process according to claim 4 or claim 9, wherein $R^2$ represents an N-protecting group which is stable to basic hydrolysis conditions.

14. A process as claimed in claim 13, wherein $R^2$ represents benzyl or $CH_2OCH_2(C_6H_5)$.

15. A process according to claim 4 or claim 9, wherein $R^3$ represents $CH_2CH_2N(CH_3)_2$ or a group of formula Ia or Ib,

* * * * *